United States Patent [19]

Lowe et al.

[11] Patent Number: 5,019,564

[45] Date of Patent: May 28, 1991

[54] NON-CLAY AGRICULTURAL GRANULE

[75] Inventors: H. Edward Lowe, Cassopolis, Mich.; Ricky L. Yoder, Elkhart; Clayton C. Nelson, Granger, both of Ind.

[73] Assignee: Edward Lowe Industries, Inc., Cassopolis, Mich.

[21] Appl. No.: 111,016

[22] Filed: Oct. 19, 1987

Related U.S. Application Data

[63] Continuation-in-part of Ser. No. 846,126, Mar. 31, 1986, abandoned.

[51] Int. Cl.⁵ .................... A01N 33/08; A01N 33/12; A01N 57/00

[52] U.S. Cl. .................... 514/75; 514/515; 514/551; 514/647; 514/673; 514/693; 514/731; 514/751; 424/413; 424/416; 71/64.13; 71/904; 71/23; 71/24; 71/DIG. 1; 71/67; 71/104; 71/126

[58] Field of Search ................. 71/64.02, 64.07, 64.13, 71/904, 23, 24, 67, 104, 126, DIG. 1; 514/75, 551; 424/413, 416

[56] References Cited

U.S. PATENT DOCUMENTS 888,148  11/1907  Dokkenwadel .................... 71/904
3,672,945  6/1972  Taylor ............................ 71/904

Primary Examiner—Ferris H. Lander
Attorney, Agent, or Firm—Thomas J. Dodd

[57] ABSTRACT

An agricultural granule capable of carrying and releasing incorporated biocidal or nutritional agricultural chemicals. The granule is formed by the agitative agglomeration of a plant fiber slurry and resembles a clay granule in all respects except for its chemical inertness.

19 Claims, No Drawings

NON-CLAY AGRICULTURAL GRANULE

CROSS-REFERENCE TO RELATED APPLICATION

This application is a continuation-in-part of application Ser. No. 846,126, filed Mar. 31, 1986 and now abandoned.

BACKGROUND OF THE INVENTION

This invention relates to an agricultural granule which can be used as a pesticide and/or fertilizer carrier or diluent, and the method of producing the agricultural granule.

The agricultural granule is well known to the agricultural crop, horticultural, and animal industries. The agricultural granule may be used as a diluent where the formulation is the dilution of the concentration of pesticide down to a level at which is will be toxic to the pest, but will not cause damage to desirable life forms and natural habitats. To those individuals knowledgeable in pesticide formulary, an agricultural granule used as a diluent is defined as a material having a low or medium sorptive capacity and is chemically inert. The agricultural granule which is used as a carrier must be capable of carrying pesticide to the site of control without any losses and then release that pesticide for control. For the agricultural granule carrier to be effective it must have high liquid holding capacity. Most typically then, the agricultural granule, dependent upon the use requirement, can be derived from clay, corn cob, vermiculite, rice hulls, and pumice, which when reduced is comprised of distinct particles within the range of 4 to 80 mesh (U.S. Standard). The agricultural granule has many advantages, the least of which includes reduced application drift due to particle weight, ease of application with accurate control of rate and placement, and the safety to the applicator and others. Since its inception in the late 1940's, the agricultural granule form of pesticide formulary has become the most widely used and most versatile of the available pesticide products. Although much work has been conducted on the formulary methods of producing the finished pesticide granule product, little has been done on altering the nature of the granule itself and its action at the site of control. This is seen through the granule pH, cation exchange capacities, sorptive capacities and moisture content, where pesticide/inert incompatibilities occur, manifested in chemical decomposition, thus rendering the pesticide ineffective. To overcome pesticide decomposition, the granule must be chemically deactivated prior to incorporation with the pesticide.

SUMMARY OF THE INVENTION

The agricultural granule of this invention overcomes the problems normally associated with conventional agricultural granules, such as varying bulk densities, varying sorptive capacities, non-controlled pesticide release rates, and pesticide decomposition. This is accomplished by creating a granule from natural fiber and water which may be formed from many different types of plant fiber as set forth in U.S. patent application Ser. Nos. 714,450 filed Mar. 21, 1985, 746,748 filed June 20, 1985 and 901,963 filed Aug. 27, 1986. Preferred, however, are the fibers derived from a primary or secondary sulfite or sulfate pulp or paper sludge, or de-inked fiber sludge. Furthermore, the method of this invention allows for the formation of an agricultural granule which resembles a clay-based granule; is highly absorbent to organic chemicals; allows accurate control of granule size, color, density, pH and other physical properties; and is chemically inert to prevent pesticide decomposition.

Accordingly, it is an object of this invention to provide for a novel agricultural granule material which can be used in formulating pesticide products for the agricultural crop, horticultural and animal industries.

Another object of this invention is to provide an agricultural granule which is economical to produce, dustless and easy to dispose of.

Another object of this invention is to provide for a paper-based agricultural granule which resembles a clay-based granule.

Another object of this invention is to provide an agricultural granule which has excellent chemical and physical properties.

Still another object of this invention is to provide for agricultural granules which can be produced to conform to the needs of the individual granule user.

Another object of this invention is to provide for a novel method of producing an agricultural granule.

Still another object of this invention is to provide for a method of producing an agricultural granule which allows accurate control of the physical properties of the absorbent.

Other objects of this invention will become apparent upon a reading of the following description.

DESCRIPTION OF THE PREFERRED EMBODIMENT

The preferred product and method herein described is not intended to be exhaustive or to limit the invention to the precise form or steps described. They are chosen and described to explain the principles of the invention and its application and practical use to enable others skilled in the art to utilize the invention.

An understanding of the agricultural granule product of this invention may be obtained by following the procedures below disclosed. The primary materials utilized are the waste materials from paper manufacture which are commonly referred to as paper sludge.

Other slurries of fibrous plant materials such as sugar beet, sugar cane, citrus pulp, grain and potato may be used. Three basic types of paper sludge which may be used are primary and secondary process sulfate or sulfite, or primary de-inked. The preferred sludge for the granule is primary de-inked sludge. Primary de-inked sludge is the waste material from recycled newsprint and other papers and normally has a content of about 40%-90% fiber and 10%-60% filler (e.g. kaolin, barytes, titanium dioxide, other plant fibers, etc.).

De-inked paper sludge in raw form is approximately 90% water. The raw sludge or slurry is analyzed for composition and bacteria. It is then dewatered by any accepted method (usually pressing or centrifuging) until it contains approximately 40%-50% solids, with 45% solids being preferred. In this dewatered stage, the paper sludge fiber is broken down or shredded by any conventional method (e.g. delumper, reduction mill or shredder) to a fiber length of 1 mm-10 mm. Such preferred equipment is a Fitzpatrick Mill or Eirich High Intensity Mixer. The preferred fiber length is 1 mm-4 mm.

The dewatered fiber then undergoes a quality adjustment if required, which may involve the addition of additives such as dye, titanium dioxide or barytes to adjust color; biocide or slimacide to control bacterial and fungal growth; and kaolin clay or barytes to increase density.

The biocide or slimacide is generally formed of one of the following: quaternary ammonium salts, aldehyde derivatives, halogenated styrenes, thiocyanates, carbamates, azo chlorides, and modified phenols. Halogenated styrenes and thiocyanates are preferred. More specifically, preferred is a mixture of bromonitrostyrene and methylene bisthiocyanate such as Slime-Trol R RX-41 sold by Betz Paperchem, Inc.

After the quality adjustment, the sludge mixture is agglomerated or granulated by agitating the slurry (wi8th added water if necessary) in an agglomeration device such as a drum pelletizer, disk pelletizer, pinmill, or granulator. Due to the lack of a separate binder, the fiber content of the solids in the mixture should exceed at least 10%-15% by weight and will preferably be as high as possible, with mineral fillers constituting the remainder. During agitation, the fibers begin to interlock and bond together to form the granules, the size of which is determined by the water/solids ratio, the time elapsed in the agglomeration device, and the fiber/filler ratio. The sludge and slurry mixture is formed into spherical pellets or, preferably, granule shapes. Should spherical pellets be formed they are flattened into a granular shape by a standard compaction device.

The product is then dried until the granule contains 1%-10% moisture by weight. Drying is accomplished in any standard dryer such as a fluid bed dryer, turbo dryer, belt dryer or tray dryer at a temperature range of 200°-750° F. After drying, color may be added for pesticide identification. The product is then packaged and sold as an agricultural granule or similar product, for the addition of biocidal or nutritional compositions.

The following examples are submitted to better understand the process and product.

EXAMPLE 1

A quantity of a primary process sulfite paper sludge with a solids content of 41.8% was baked in a tray oven at 250° F. until a sludge moisture content of 48% was obtained. The sludge was then placed in an Eirich High Intensity Mixer which separated and chopped the fibers to a workable size, while a corn starch binder was admixed into the product at 1% binder by total weight of product. No additional density modifiers, coloring agents, or biocides were added. The sludge was then placed in a lab discpelletizer and agitated until granules of 16/30 U.S. Standard mesh size were formed. The granules were then dried and their physical properties tested to obtain the following data:

| Bulk Density | 31.6 lbs/cft. |
|---|---|
| Moisture Content | 2% |
| Water Absorbency | .85 ml/gm |
| Oil Absorbency | .64 ml/gm |
| pH | 6.25 |
| Attrition Resistance | 99.0% |
| LHC (glycerol) | 27.1% |

| Screen Analysis | |
|---|---|
| Mesh | % Retained |
| +16 | 0.17 |
| 18 | 10.32 |
| 20 | 33.10 |
| 25 | 22.34 |
| 30 | 19.94 |
| 35 | 10.69 |
| 40 | 3.02 |
| −40 | 0.42 |

The sample was then sent to Eli Lilly Research Laboratories for evaluation as a carrier for insecticide in controlling fire ants.

EXAMPLE 2

De-inked sludge from Georgia-Pacific Corporation was subjected to the same process as defined in Example 1 with the exception that no binder was added to the sludge during fiber separation and chopping. The granules formed were of slightly smaller size (24/48 mesh) and bulk density ( 40 lbs/cft.). The granules thus formed were found to be nearly inert chemically, and had an LHC of about 25%.

EXAMPLE 3

A combination of de-inked sludge and primary sulfite sludge was processed according to the method of Example 1. It was discovered that bulk density could be varied from between 25-42 lbs/cft., and LHC capacities increased with higher proportions of sulfite sludge.

EXAMPLE 4

A quantity of de-inked sludge from Fort Howard Paper Company was fed into a Franklin Miller De-lumper for shedding, then conveyed to a Fitzpatrick Fitzmill for completion of shredding. The sludge was then conveyed to a Mars Mineral Pin Mill where granules were formed. Other operations may also be performed at this stage, if necessary, such as density modification, addition of biocides, and control of size. After agglomeration, the granules were conveyed to a Carrier 3 State Fluid Bed Dryer for drying and air classification and then finally conveyed to a Sweeco Separator for screening. The granules formed were then tested as carriers for both organophosphate and carbamate pesticides, compounds which normally become very unstable when carried by clay granules.

Sample 102 - 20% Organophosphate on 12/24 mesh product
Sample 103 - 20% Organophosphate on 24/48 mesh product
Sample 104 - 15% Carbamate on 12/24 mesh product
Sample 105 - 15% Carbamate on 24/48 mesh product

| Age | Room Temp | 50° C. |
|---|---|---|
| | Sample 102 | |
| Initial | 19.3 | — |
| 1 Month | 19.3 | 20.3 |
| 3 Months | 19.9 | — |
| Sample 103 | | |
| Initial | 18.9 | — |
| 1 Month | 21.0 | 20.2 |
| 3 Months | 19.6 | 19.7 |
| Sample 104 | | |
| Initial | 14.8 | — |
| 1 Month | 13.9 | 13.0 |
| 3 Months | 13.6 | 12.7 |
| Sample 105 | | |
| Initial | 15.5 | — |
| 1 Month | 14.6 | 15.0 |
| 3 Months | 14.4 | 13.2 |

It has been noted that the fiber content of the solids should be at least 10%-15%. This percentage was determined through testing performed according to ASTM method D-1102, which determines the ash content in wood. Statistics indicate that increased fiber content results in lowered ash content according to the test calculations which are reprinted below. A series of experiments according to ASTM D-1102 were performed upon granules formed according to the above disclosed method, which granules contained from 0% fiber to 100% fiber by weight in 10% increments. Experiments were also performed on granules having from 6-9% fiber in 1% increments. The test results are reprinted below.

Calculations:
1. Actual Ash Content: Ash (%) = W1/W2 × 100
   ASTM Method D-1102  W1 = weight of Ash
   W2 = weight of oven-dry sample
2. Expected Ash Content: (% Ash F1) × (% F1 in sample) = EAF1
   (% Ash F2) × (% F2 in sample) = EAF2
   EAF1 + EAF2 = Total expected ash content of sample.
   F1 = Filler
   F2 = Fiber
   EAF1 = Expected ash content of filler
   EAF2 = Expected ash content of fiber

TEST RESULTS

| Fiber Content (%) | Filler Content (%) | Expected Ash Content (%) | Actual Ash Content (%) |
|---|---|---|---|
| 100 | 0 | 25.2 | 25.2 |
| 90 | 10 | 31.64 | 31.95 |
| 80 | 20 | 38.08 | 39.4 |
| 70 | 30 | 44.52 | 45.19 |
| 60 | 40 | 50.96 | 50.82 |
| 50 | 50 | 57.40 | 56.09 |
| 40 | 60 | 63.84 | 67.83 |
| 30 | 70 | 70.28 | 69.42 |
| 20 | 80 | 76.72 | 74.61 |
| 15 | 85 | 79.9 | 78.18 |
| 10 | 90 | 83.16 | 78.32 |
| 9 | 91 | 83.38 | 77.25 |
| 8 | 92 | 84.4 | 79.22 |
| 7 | 93 | 85.1 | 77.28 |
| 6 | 94 | 85.6 | 75.54 |
| 5 | 95 | 86.4 | 77.09 |
| 0 | 100 | 89.6 | 89.6 |

Tests were also conducted on each of the granules to determined attrition rate, size, bulk density, and absorbency, which results are reprinted below.

ATTRITION DATA

| Fiber/Filler % | Resistance to Attrition |
|---|---|
| 100/0 | 99.96% |
| 90/10 | 99.80% |
| 80/20 | 99.70% |
| 70/30 | 99.30% |
| 60/40 | 99.10% |
| 50/50 | 99.40% |
| 40/60 | 98.80% |
| 30/70 | 91.60% |
| 20/80 | 92.62% |
| 10/90 | 88.60% |
| 100/0 | 48.30% |

SCREEN ANALYSIS DATA

| Fiber/Filler (%) | +6 Mesh (%) | −60 Mesh (%) |
|---|---|---|
| 100/0 | .42 | .76 |
| 90/10 | 1.08 | .40 |
| 80/20 | .87 | .46 |
| 70/30 | 1.09 | .34 |
| 60/30 | 2.08 | 1.03 |
| 50/50 | 6.24 | .48 |
| 40/60 | 8.74 | .40 |
| 30/70 | 18.53 | 1.18 |
| 20/80 | 44.62 | 4.72 |
| 10/90 | 1.41 | 10.06 |

| | FIBER/FILLER RATIO | | | | | | | | | |
|---|---|---|---|---|---|---|---|---|---|---|
| | 100/0 | 90/10 | 80/20 | 70/30 | 60/40 | 50/50 | 40/60 | 30/70 | 20/80 | 10/90 |
| Screen Analysis/U.S. Mesh % Retained | | | | | | | | | | |
| 6 | .42 | 1.08 | .87 | 1.09 | 2.08 | 6.24 | 8.74 | 18.53 | 44.62 | 1.41 |
| 8 | 1.02 | 1.00 | 6.13 | 2.93 | 2.82 | 11.07 | 24.76 | 37.94 | 22.36 | 8.32 |
| 12 | 8.19 | 7.04 | 22.46 | 17.33 | 10.41 | 32.50 | 32.45 | 21.34 | 6.97 | 14.64 |
| 20 | 67.36 | 70.26 | 59.72 | 65.21 | 64.36 | 41.24 | 29.99 | 15.23 | 13.88 | 46.49 |
| 30 | 14.94 | 14.68 | 7.38 | 9.17 | 12.86 | 6.09 | 1.98 | 3.08 | 4.39 | 8.23 |
| 40 | 5.86 | 4.57 | 2.14 | 2.42 | 4.64 | 1.53 | 1.08 | 1.91 | 2.08 | 6.27 |
| 60 | 1.43 | .98 | .86 | .69 | 1.80 | .85 | .61 | .80 | .98 | 4.59 |
| −60 | .76 | .40 | .46 | .34 | 1.03 | .48 | .40 | 1.18 | 4.72 | 10.06 |
| Bulk Density (lbs./cft.) | 20.59 | 22.57 | 22.25 | 19.67 | 21.35 | 23.71 | 22.86 | 20.17 | 22.88 | 18.35 |
| Water Abs. (%) | 131 | 128 | 116 | 123 | 129 | 112 | 108 | 110 | 103 | 100 |
| Moisture (%) | 3.81 | 4.81 | 3.15 | 2.96 | 4.06 | 7.62 | 5.84 | 5.15 | 2.09 | 6.0 |
| Resistance to Attrition (%) | 99.96 | 99.8 | 99.7 | 99.3 | 99.1 | 99.4 | 98.8 | 91.6 | 92.62 | 88.6 |

NOTE:
Granular products formed with less than 10% fiber broke down during screen analysis.

It was further noted that below 15% fiber content, two distinct granules were formed. At 10% fiber the first type of granule was a fiber/filler mixture having 78.32% ash, below the expected ash content of a homogenous granule. The second type of granule is a white, very soft granule having 87.9% ash, which indicates it is almost entirely comprised of filler (expected ash content of 100% filler is 89.6%).

At 10% fiber and below granule formation is very poor and produces a quantity of fine powder residue having between 87-88.6% ash. Attrition rates also increase as fiber content decreases, and at less than 10% fiber, granules were often too friable to obtain accurate attrition data. Finally, the percentage of fines (granules of less than 60 Mesh) obtained remained fairly constant from 100% fiber down to 40% then increased markedly. Fines contained about 89.1% or almost entirely filler.

It is understood that the invention is not limited to the details above-given, but may be modified within the scope of the following claims:

We claim:

1. An agricultural granule adapted for carrying an incorporated chemical, said granule comprising 10-100% plant fiber and from 0-90% of a mineral filler, said granule being substantially inert with regard to said incorporated chemical, said plant fibers forming interlocking bonds to form said granule without requiring a separate chemical binder.

2. The filler material of claim 1 wherein said granulated plant fiber is one of the group of materials which consists of citrus pulp, sugar cane, sugar beets, potatoes, grain and paper sludge.

3. The agricultural granule of claim 2 wherein said plant fiber is primary de-inked paper sludge having from 40%-90% fiber by weight.

4. The filler material of claim 1 and an incorporated biocide for controlling bacteria and fungi in said granulated plant fiber.

5. The filler material of claim 1 wherein said filler material is of a granular composition ranging from 12 to 48 mesh size.

6. A method of producing a granule capable of carrying agricultural chemicals comprising the steps of:
   a) providing a quantity of plant fiber slurry wherein the slurry includes at least 10% by weight of the plant fiber;
   b) adjusting the moisture content of said slurry to allow fiber size reduction;
   c) reducing the fiber size of said slurry;
   d) agitating said slurry in the absence of separate chemical binders whereupon said plant fibers interlock and bond to form granules which are substantially chemically inert; and
   e) drying said granules.

7. The method of claim 6 wherein step a) includes providing a quantity of paper sludge having 40%-90% fiber content by weight.

8. The method of claim 6 and a step g) of adding a dye to adjust the color of said mixture.

9. The method of claim 8 and a step h) of adding a biocide to said mixture.

10. The method of claim 9 and an additional step i) of packaging said granules.

11. The method of claim 10 and a step j) of incorporating an agricultural chemical into said granules.

12. The method of claim 11 wherein step j) includes incorporating an organophosphate pesticide into said granules.

13. The method of claim 6 wherein step a) includes providing a quantity of primary de-inked paper sludge having 40%-90% fiber content by weight.

14. The method of claim 6 wherein step e) includes agglomerating said mixture in a disk pelletizer.

15. The method of claim 6 wherein step e) includes agglomerating said mixture in a pinmill.

16. The method of claim 6 wherein step d) includes reducing the fiber size of said mixture to a range of 1 mm-10 mm in length.

17. The method of claim 6 wherein step d) includes shredding said mixture in a high intensity mixer.

18. The method of claim 6 wherein step j) includes incorporating a carbamate pesticide into said granules.

19. The method of claim 6 wherein step d) includes agitating said slurry in the absence of a chemical binder.

* * * * *